United States Patent
Giles et al.

(10) Patent No.: US 9,552,970 B2
(45) Date of Patent: Jan. 24, 2017

(54) TIME SHIFT FOR IMPROVED ION MOBILITY SPECTROMETRY OR SEPARATION DIGITISATION

(71) Applicant: Micromass UK Limited, Wilmslow (GB)

(72) Inventors: Kevin Giles, Stockport (GB); David J. Langridge, Macclesfield (GB); Keith Richardson, Derbyshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/772,448

(22) PCT Filed: Mar. 5, 2014

(86) PCT No.: PCT/GB2014/050642
§ 371 (c)(1),
(2) Date: Sep. 3, 2015

(87) PCT Pub. No.: WO2014/135865
PCT Pub. Date: Sep. 12, 2014

(65) Prior Publication Data
US 2016/0027627 A1 Jan. 28, 2016

(30) Foreign Application Priority Data

Mar. 6, 2013 (EP) ..................... 13158040
Mar. 6, 2013 (GB) ................... 1304039.9

(51) Int. Cl.
*H01J 49/40* (2006.01)
*H01J 49/00* (2006.01)
*G01N 27/62* (2006.01)

(52) U.S. Cl.
CPC ......... *H01J 49/0031* (2013.01); *G01N 27/622* (2013.01); *H01J 49/401* (2013.01)

(58) Field of Classification Search
CPC combination set(s) only.
See application file for complete search history.

(56) References Cited

U.S. PATENT DOCUMENTS

| 6,559,441 B2 | 5/2003 | Clemmer |
| 6,992,283 B2 | 1/2006 | Bateman et al. |

(Continued)

FOREIGN PATENT DOCUMENTS

| GB | 2391697 | 2/2004 |
| GB | 2397433 | 7/2004 |

(Continued)

*Primary Examiner* — Phillip A Johnston
*Assistant Examiner* — Hsien Tsai
(74) *Attorney, Agent, or Firm* — Diederiks & Whitelaw, PLC (57) ABSTRACT

A method of analyzing ions is disclosed comprising: (i) separating ions according to a physico-chemical property in a separator; (ii) transmitting ions which emerge from the separator through a transfer device with a first transit time t1, energizing a pusher electrode or orthogonal acceleration electrode and obtaining first data; (iii) transmitting ions which subsequently emerge from the separator through the transfer device with a second greater transit time t2, energizing the pusher electrode or orthogonal acceleration electrode and obtaining second data; and (iv) repeating steps (ii) and (iii) one or more times. The pusher electrode or orthogonal acceleration electrode is energized with a period t3, wherein t2-t1 is arranged to equal t3/2. The first and second data are combined to form a composite data set.

16 Claims, 5 Drawing Sheets

(56) References Cited

U.S. PATENT DOCUMENTS

| | | | |
|---|---|---|---|
| 8,653,446 B1* | 2/2014 | Mordehai | G01N 27/622 |
| | | | 250/281 |
| 2003/0001084 A1 | 1/2003 | Bateman et al. | |
| 2003/0001087 A1* | 1/2003 | Fuhrer | H01J 49/004 |
| | | | 250/287 |
| 2004/0026613 A1* | 2/2004 | Bateman | H01J 49/062 |
| | | | 250/281 |
| 2007/0278397 A1 | 12/2007 | Bateman et al. | |
| 2009/0294642 A1* | 12/2009 | Brown | H01J 49/0031 |
| | | | 250/282 |
| 2010/0128246 A1 | 5/2010 | Heizmann et al. | |
| 2011/0062323 A1* | 3/2011 | Brown | H01J 49/0072 |
| | | | 250/282 |

FOREIGN PATENT DOCUMENTS

| | | |
|---|---|---|
| GB | 2409764 | 7/2005 |
| GB | 2421840 | 7/2006 |
| GB | 2451149 | 1/2009 |
| GB | 2485667 | 5/2012 |
| GB | 2497948 | 7/2013 |
| WO | 02/097383 | 12/2002 |

\* cited by examiner

FIG. 5 ize patent application No. 1304039.9 filed on 6 Mar. 2013 and European patent application No. 13158040.9 filed 6 Mar. 2013. The entire contents of these applications are incorporated herein by reference.

TIME SHIFT FOR IMPROVED ION MOBILITY SPECTROMETRY OR SEPARATION DIGITISATION

CROSS-REFERENCE TO RELATED APPLICATION

This application is the National Stage of International Application No. PCT/GB2014/050642, filed 5 Mar. 2014 which claims priority from and the benefit of United Kingdom patent application No. 1304039.9 filed on 6 Mar. 2013 and European patent application No. 13158040.9 filed 6 Mar. 2013. The entire contents of these applications are incorporated herein by reference.

BACKGROUND OF THE PRESENT INVENTION

The present invention relates to a method of analysing ions, a method of mass spectrometry, an analytical device and a mass spectrometer.

U.S. Pat. No. 6,992,283 (Micromass) discloses an arrangement wherein ions are passed through an ion mobility separator and are then mass analysed by a Time of Flight mass analyser.

It is known to perform asynchronous IMS-Time of Flight acquisitions wherein the Time of Flight experimental time determines the ion mobility spectrometry or separation digitisation rate.

One problem with conventional mass spectrometers comprising an ion mobility separator or spectrometer in combination with a Time of Flight mass analyser is that the effective digitisation of an ion peak eluting from an ion mobility spectrometry or separation device by the Time of Flight mass analyser may be limited.

It is known to synchronise an orthogonal acceleration Time of Flight pusher with the release of ions into an ion mobility spectrometry or separation device. This approach is, however, limited by the need to accurately synchronise the pusher and ion mobility spectrometry or separation cycle times and requires additional electronics. This approach also introduces the possibly of additional systematic errors in mobility calibration due to any lack of synchronicity.

FIG. 10 of US 2011/0062323 (Micromass) discloses an arrangement comprising an ion mobility separator 26 and a collision cell 27 arranged downstream of the ion mobility separator 26. It is contemplated that the collision cell 27 may comprise an Electron Transfer Dissociation ("ETD") collision cell. The collision cell 27 comprises a plurality of ring electrodes and an arrangement is contemplated wherein travelling or transient DC voltages are applied to the ring electrodes and a feedback control mechanism is used to control the effective velocity at which the transient DC voltages are translated along the length of the collision cell 27 in order to optimise the Electron Transfer Dissociation fragmentation and charge reduction process.

US 2003/0001087 (Fuhrer) discloses a time of flight mass spectrometer for monitoring fast processes using an interleaved timing scheme and a position sensitive detector.

US 2007/0278397 (Micromass) discloses providing an ion guide downstream of an ion mobility spectrometer. A plurality of axial potential wells are created in the ion guide to maintain the fidelity of ions received from the ion mobility spectrometer.

US 2010/0128246 (Heizmann) discloses an optoelectronic sensor for the measurement of distances.

GB-2497948 (Makarov) discloses a collision cell for tandem mass spectrometry.

GB-2391697 (Micromass) discloses a mass spectrometer having an ion guide which receives ions and emits ions in a synchronised manner with an orthogonal acceleration Time of Flight mass analyser.

GB-2397433 (Micromass) discloses a mass spectrometer wherein ions from a pulsed ion source are received by an ion guide in which multiple trapping regions are created.

GB-2451149 (Micromass) discloses a dual mode ion mobility mass analyser device.

GB-2421840 (Micromass) discloses a mass spectrometer comprising an ion guide located downstream of an ion mobility spectrometer.

GB-2485667 (Micromass) discloses a mass spectrometer comprising a gas phase ion-neutral reaction device arranged to perform Hydrogen-Deuterium exchange.

It is desired to provide an improved mass spectrometer and method of mass spectrometry.

SUMMARY OF THE PRESENT INVENTION

According to an aspect of the present invention there is provided a method of analysing ions comprising:

(i) separating ions according to a physico-chemical property in a separator;

(ii) transmitting ions which emerge from the separator through a transfer device with a first transit time t1, energising a pusher electrode or orthogonal acceleration electrode and obtaining first data;

(iii) transmitting ions which subsequently emerge from the separator through the transfer device with a second greater transit time t2, energising the pusher electrode or orthogonal acceleration electrode and obtaining second data; and (iv) repeating steps (ii) and (iii) one or more times;

wherein the method preferably further comprises:

preferably energising the pusher electrode or orthogonal acceleration electrode with a period t3, wherein t2-t1 is arranged to equal t3/n and wherein n=2; and preferably combining the first and second data to form a composite data set.

US 2011/0062323 (Micromass) does not disclose repeatedly switching the transit time of ions which emerge from a separator through a transfer device, energising a pusher electrode each time and obtaining mass spectral data each time and combining the mass spectral data to form a composite data set.

Furthermore, US 2011/0062323 (Micromass) does not disclose increasing the drift time by a time which is equal to half the pusher period.

The present invention relates to improving the digitisation of the ion mobility spectrometry or separation space without compromising Time of Flight performance.

The preferred embodiment relates to a method of time shift for improved ion mobility spectrometry or separation digitisation and is a new mode of operation for existing instrument geometries and future novel instrument geometries.

The present invention provides the capability to improve the effective digitisation of fast time dispersive processes such as ion mobility separations by introducing a predetermined time shift to the drift time of some of the ions and compensating or calibrating for this shift before combining this data with un-shifted data.

A preferred embodiment of the present invention comprises an ion separation device such as an ion mobility separator ("IMS") followed by a transfer device such as a travelling wave ion guide ("TWIG") that acts to maintain the fidelity of the ion mobility separation whilst also being able to introduce a known and programmable delay in the transit time of some ions through the entire system. The transfer device or travelling wave ion guide is preferably followed by a fragmentation device. An orthogonal acceleration Time of Flight ("oa-ToF") mass analyser is preferably provided downstream and preferably acts as the digitisation mechanism.

State of the art instruments that employ ion mobility spectrometry or separation devices coupled to a Time of Flight mass analyser are limited to digitisation times that correspond with at least the length of time of the orthogonal acceleration time of flight period.

According to the preferred embodiment the pusher electrode or orthogonal acceleration electrode is energised with a period t3, wherein t2-t1=t3/2 i.e. the increase in transit time t2-t1 is arranged to be half a time bin or half the pusher period. However, other less preferred embodiments are contemplated wherein the pusher electrode or orthogonal acceleration electrode is energised with a period t3, wherein t2-t1=t3/n and wherein n≥2. In particular, embodiments are contemplated wherein n=3, 4, 5, 6, 7, 8, 9, 10, 11, 12, 13, 14, 15, 16, 17, 18, 19, 20 or >20. According to an embodiment n is preferably arranged to be an integer. However, other embodiments are contemplated wherein n is a fraction.

According to an embodiment n may comprise a value within one of the following ranges: 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-50, 50-100, 100-500, 500-1000 or >1000.

The physico-chemical property preferably comprises ion mobility or differential ion mobility.

The physico-chemical property preferably comprises mass or mass to charge ratio.

According to another aspect of the present invention there is provided an analytical device comprising:

a separator for separating ions according to a physico-chemical property;

a transfer device;

a pusher electrode or orthogonal acceleration electrode;

an analyser; and a control system arranged and adapted:

(i) to cause ions to separate according to a physico-chemical property in the separator;

(ii) to transmit ions which emerge from the separator through the transfer device with a first transit time t1, to energise the pusher electrode or orthogonal acceleration electrode and to analyse the ions with the analyser to obtain first data;

(iii) to transmit ions which subsequently emerge from the separator through the transfer device with a second greater transit time t2, to energise the pusher electrode or orthogonal acceleration electrode and to analyse the ions with the analyser to obtain second data; and (iv) to repeat steps (ii) and (iii) one or more times;

wherein the control system is preferably further arranged and adapted:

preferably to energise the pusher electrode or orthogonal acceleration electrode with a period t3, wherein t2-t1 is arranged to equal t3/n and wherein n=2; and preferably to combine the first and second data to form a composite data set.

The separator preferably comprises an ion mobility spectrometer, a differential ion mobility spectrometer or other separation device.

The separator preferably comprises a device for separating ions according to their mass or mass to charge ratio.

The analytical device preferably further comprises a device arranged and adapted to pulse ions into the separator.

The analyser preferably comprises an orthogonal acceleration Time of Flight mass analyser having a pusher electrode or an orthogonal acceleration electrode.

The pusher electrode or orthogonal acceleration electrode is preferably energised asynchronously with respect to the separator.

The pusher electrode or orthogonal acceleration electrode is preferably energised with a period t3, wherein t2-t1 is arranged to equal half of the period tb3.

According to another aspect of the present invention there is provided a mass spectrometer comprising an analytical device as described above.

According to another aspect of the present invention there is provided a method of analysing ions comprising:

(i) separating ions according to a physico-chemical property in a separator;

(ii) transmitting ions which emerge from the separator through a first ion path with a first transit time t1, energising a pusher electrode or orthogonal acceleration electrode and obtaining first data; and (iii) transmitting ions which subsequently emerge from the separator through a second different ion path with a second greater transit time t2, energising the pusher electrode or orthogonal acceleration electrode and obtaining second data; and (iv) repeating steps (ii) and (iii) one or more times;

wherein the method preferably further comprises:

preferably energising the pusher electrode or orthogonal acceleration electrode with a period t3, wherein t2-t1 is arranged to equal t3/n and wherein n=2; and preferably combining the first and second data to form a composite data set.

According to another aspect of the present invention there is provided a method of mass spectrometry comprising a method as described above.

According to another aspect of the present invention there is provided an analytical device comprising:

a separator for separating ions according to a physico-chemical property;

a transfer device;

a pusher electrode or orthogonal acceleration electrode;

an analyser; and a control system arranged and adapted:

(i) to cause ions to separate according to a physico-chemical property in the separator;

(ii) to transmit ions which emerge from the separator through a first ion path through the transfer device with a first transit time t1, to energise the pusher electrode or orthogonal acceleration electrode and to analyse the ions with the analyser to obtain first data;

(iii) to transmit ions which subsequently emerge from the separator through a second different ion path through the transfer device with a second greater transit time t2, to energise the pusher electrode or orthogonal acceleration electrode and to analyse the ions with the analyser to obtain second data; and (iv) to repeat steps (ii) and (iii) one or more times;

wherein the control system is preferably further arranged and adapted:

preferably to energise the pusher electrode or orthogonal acceleration electrode with a period t3, wherein t2-t1 is arranged to equal t3/n and wherein n=2; and preferably to combine the first and second data to form a composite data set.

According to another aspect of the present invention there is provided a method of analysing ions comprising:

(i) separating ions according to a physico-chemical property in a separator during a first cycle of separation and transmitting ions which emerge from the separator through a transfer device with a first transit time t1, energising a pusher electrode or orthogonal acceleration electrode and obtaining first data;

(ii) separating ions according to the physico-chemical property in the separator during a second separate cycle of separation and transmitting ions which subsequently emerge from the separator through the transfer device with a second greater transit time t2, energising a pusher electrode or orthogonal acceleration electrode and obtaining second data; and (iii) repeating steps (i) and (ii) one or more times;

wherein the method preferably further comprises:

preferably energising the pusher electrode or orthogonal acceleration electrode with a period t3, wherein t2-t1 is arranged to equal t3/n and wherein n=2; and preferably combining the first and second data to form a composite data set.

According to another aspect of the present invention there is provided an analytical device comprising:

a separator for separating ions according to a physico-chemical property;

a transfer device;

a pusher electrode or orthogonal acceleration electrode;

an analyser; and a control system arranged and adapted:

(i) to cause ions to separate according to a physico-chemical property in the separator during a first cycle of separation, to energise the pusher electrode or orthogonal acceleration electrode and to transmit ions which emerge from the separator through the transfer device with a first transit time t1 and to analyse the ions with the analyser to obtain first data;

(ii) to cause ions to separate according to a physico-chemical property in the separator during a second separate cycle of separation, to energise the pusher electrode or orthogonal acceleration electrode and to transmit ions which subsequently emerge from the separator through the transfer device with a second greater transit time t2 and to analyse the ions with the analyser to obtain second data; and (iii) to repeat steps (i) and (ii) one or more times;

wherein the control system is preferably further arranged and adapted:

preferably to energise the pusher electrode or orthogonal acceleration electrode with a period t3, wherein t2-t1 is arranged to equal t3/n and wherein n=2; and preferably to combine the first and second data to form a composite data set.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infra-red radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Historically, the timescales associated with liquid/gas chromatography, ion mobility spectrometry or separation ("IMS") and orthogonal acceleration Time of Flight mass analysis have been well matched allowing many ion mobility spectrometry or separation experiments to be performed per chromatographic peak and many Time of Flight analyses to be performed per ion mobility separation peak. This in turn has enabled multidimensional nested data sets to be obtained with minimal compromise to each of the separations. This has allowed the development of multiple instrument geometries incorporating a LC-IMS-ToF mass analyser geometry.

In these arrangements an orthogonal acceleration Time of Flight mass analyser acts as both a mass spectrometer and also as an effective way of digitising the ion mobility peaks. The effective digitisation period is equal to the drift time through the orthogonal acceleration Time of Flight mass analyser.

The above described conventional approach is currently adequate on most state of the art instruments. However, it is apparent that the desire to increase the resolution of ion mobility spectrometry or separation devices coupled with the desire to increase the resolution of orthogonal acceleration Time of Flight mass analysers are in conflict as improvements in ion mobility spectrometry or separation resolution will lead to shorter ion mobility spectrometry or separation temporal peaks widths whilst improvements in orthogonal acceleration time of flight resolution will lead to extended orthogonal acceleration time of flight times. Accordingly, these two development directions are in conflict and will most likely lead to a mismatch or divergence between ion mobility spectrometry or separation and orthogonal acceleration time of flight timescales with the ion mobility spectrometry or separation temporal peak widths (and consequentially ion mobility spectrometry or separation resolution) being limited by the orthogonal acceleration time of flight experimental time.

Extending ion mobility spectrometry or separation experimental times can alleviate this somewhat but ultimately the same problem occurs between ion mobility spectrometry or separation experimental time and chromatographic temporal peak widths.

The present invention seeks to improve the effective digitisation of ion mobility spectrometry or separation peaks without compromising the experimental time of the orthogonal acceleration Time of Flight mass analyser.

A known method of improving the effective digitisation of ion mobility spectrometry or separation peaks is to reduce the orthogonal acceleration Time of Flight cycle time to represent just the range of time of flights of the ions within the pusher region at that particular moment. This allows a significant reduction in the orthogonal acceleration time of flight experimental time and ultimately improves the digitisation of the ion mobility spectrometry or separation peaks. However, whilst this approach can work well for IMS-Time of Flight it relies upon there being a strong correlation between the mass to charge ratio range of ions in the pusher region and the ion mobility spectrometry or separation drift time. Such an approach is therefore of limited use for weakly correlated mass to charge ratio-ion mobility drift time distributions such as those experienced with proteomics experiments or those found in post ion mobility spectrometry or separation fragmentation experiments.

Figure 1:
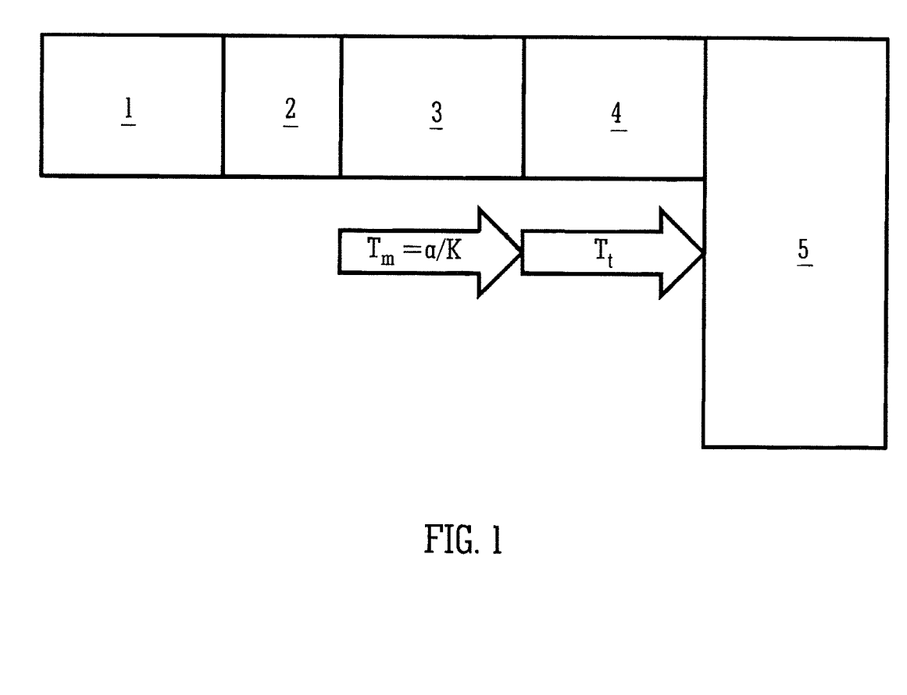
FIG. 1 shows a mass spectrometer according to an embodiment of the present invention wherein ions emerging from an ion mobility spectrometry or separation device are arranged to transit through a travelling wave ion guide prior to being analysed by an orthogonal acceleration Time of Flight mass analyser.

FIG. 1 shows a simplified schematic of a mass spectrometer according to a preferred embodiment which may be utilised to perform the present invention. FIG. 1 is for illustrative purposes only and is not intended to restrict the geometries that the present invention can be employed on.

In the embodiment shown in FIG. 1 ions from an ion source 1 are periodically released into an ion mobility spectrometry or separation ("IMS") device 3 from a pre-IMS accumulation region 2. The average time taken by an ion to traverse the ion mobility spectrometry or separation region 3 is inversely proportional to the mobility K of the ion for a linear drift tube ion mobility spectrometry or separation device. The constant of proportionality a is related to the electric field strength, the drift tube length, pressure and temperature etc.

After exiting the ion mobility spectrometry or separation region 3 the ions cross or transit through a transfer region or transfer device 4 such as an RF confined travelling wave ion guide ("TWIG") before entering an orthogonal acceleration Time of Flight mass analyser 5. The time taken to cross or transit through the travelling wave ion guide 4 is, to a first approximation, related to the travelling wave speed and the length of the transfer region 4.

After entering the orthogonal acceleration Time of Flight mass analyser 5 the ion beam is preferably periodically sampled by a pusher electrode operating asynchronously with the release of ions into the ion mobility spectrometry or separation 3. Ignoring axial time of flight effects, the time taken by an ion to reach the pusher region is approximated by a/K+b. Each push or orthogonal acceleration event is time assigned a drift time or bin number.

Figure 2:
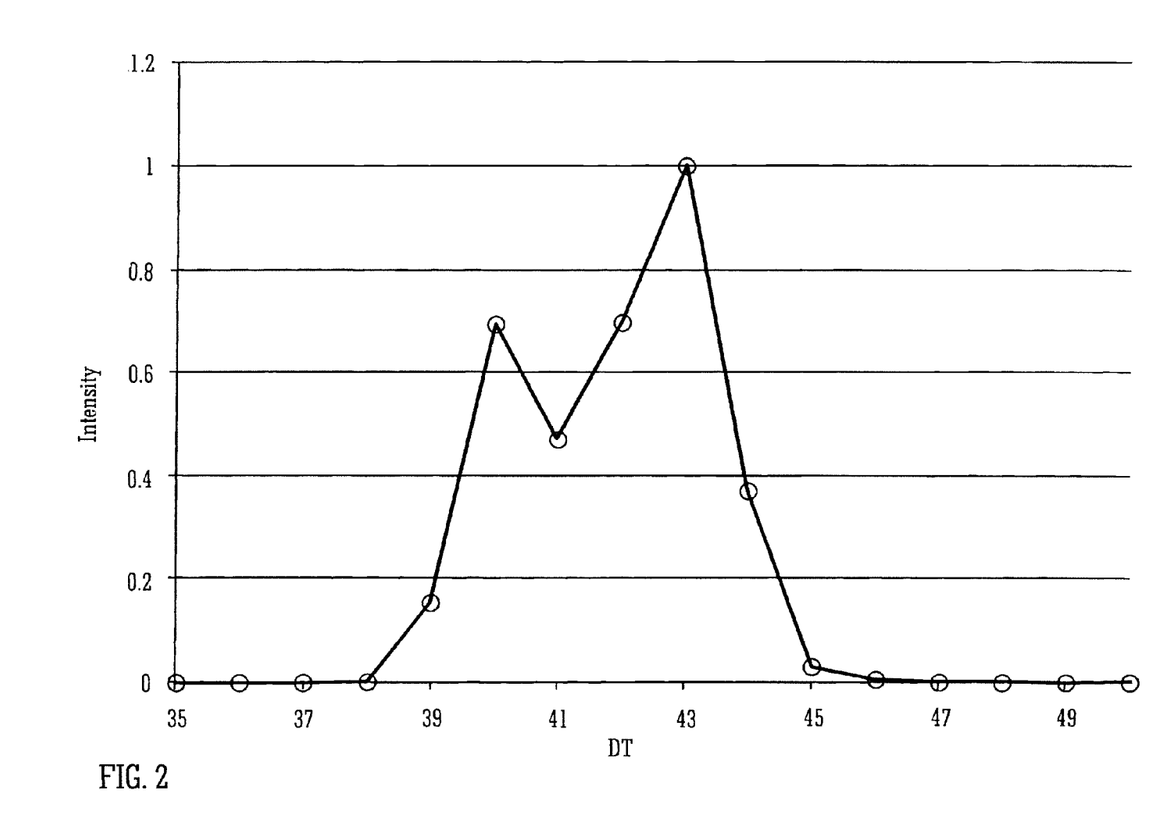
FIG. 2 shows an ion mobility drift peak as effectively digitised by a conventional orthogonal acceleration Time of Flight mass analyser.

This mode of operation by itself produces data similar to that shown in FIG. 2 wherein each drift time point corresponds with a complete mass to charge ratio spectrum. The intensity value in FIG. 2 has been normalised. For illustrative purposes the digitisation of the ion mobility spectrometry or separation peak by the Time of Flight mass analyser 5 has been deliberately arranged so that the ion mobility spectrometry or separation peak is effectively under digitised.

It should be understood that the Time of Flight mass analyser which is repeatedly sampling the ion mobility peak as shown in FIG. 2 can not effectively be operated any faster.

Figure 3:
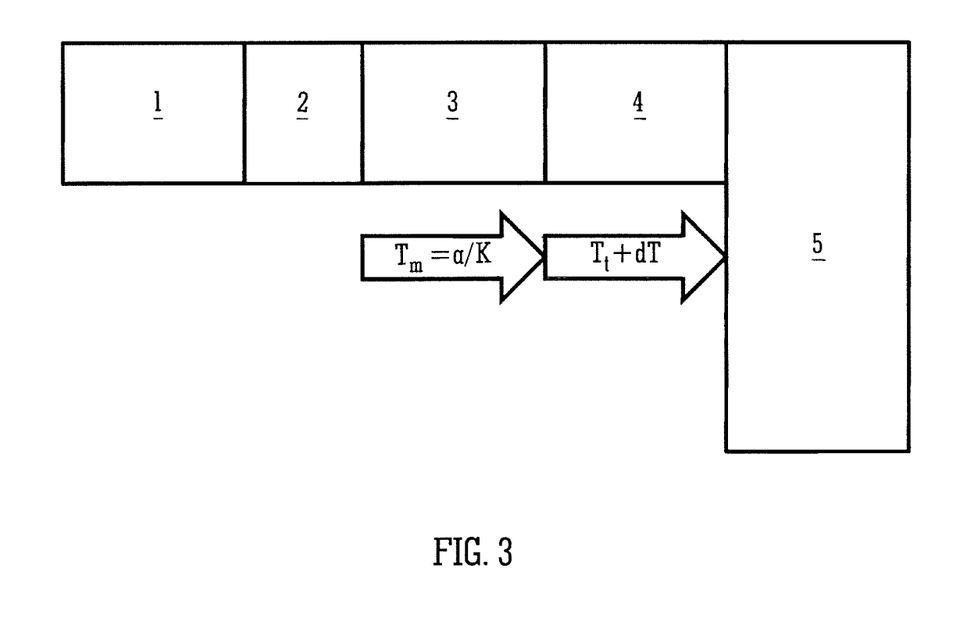
FIG. 3 illustrates a preferred embodiment wherein some ions transiting through a transit device are subjected to a delay.

FIG. 3 illustrates an important aspect of the preferred embodiment wherein the mass spectrometer is operated the same as previously described (i.e. the pusher electrode is operated at the same frequency as before) with the exception that the time taken to traverse the transfer region or transfer device 4 is increased by a value dT which is equal to half the pusher period. As a result, the arrival time of ions at the orthogonal acceleration Time of Flight mass analyser 5 will be shifted by half a pusher period. Increasing the time taken to cross or traverse the transfer region or transfer device 4 may be achieved by altering the travelling wave speed of the travelling wave ion guide 4. The travelling wave preferably acts on all ions independent of their ion mobility or their mass to charge ratio.

As a result 'half bin' different drift time values may be assigned to the shifted data based on the half pusher period shift. According to an embodiment 50% of the mass spectral data may be acquired with a time shift and 50% of the mass spectral data may be acquired without a time shift. The two mass spectral data sets may then be combined resulting in data similar to that shown in FIG. 4.

Figure 4:
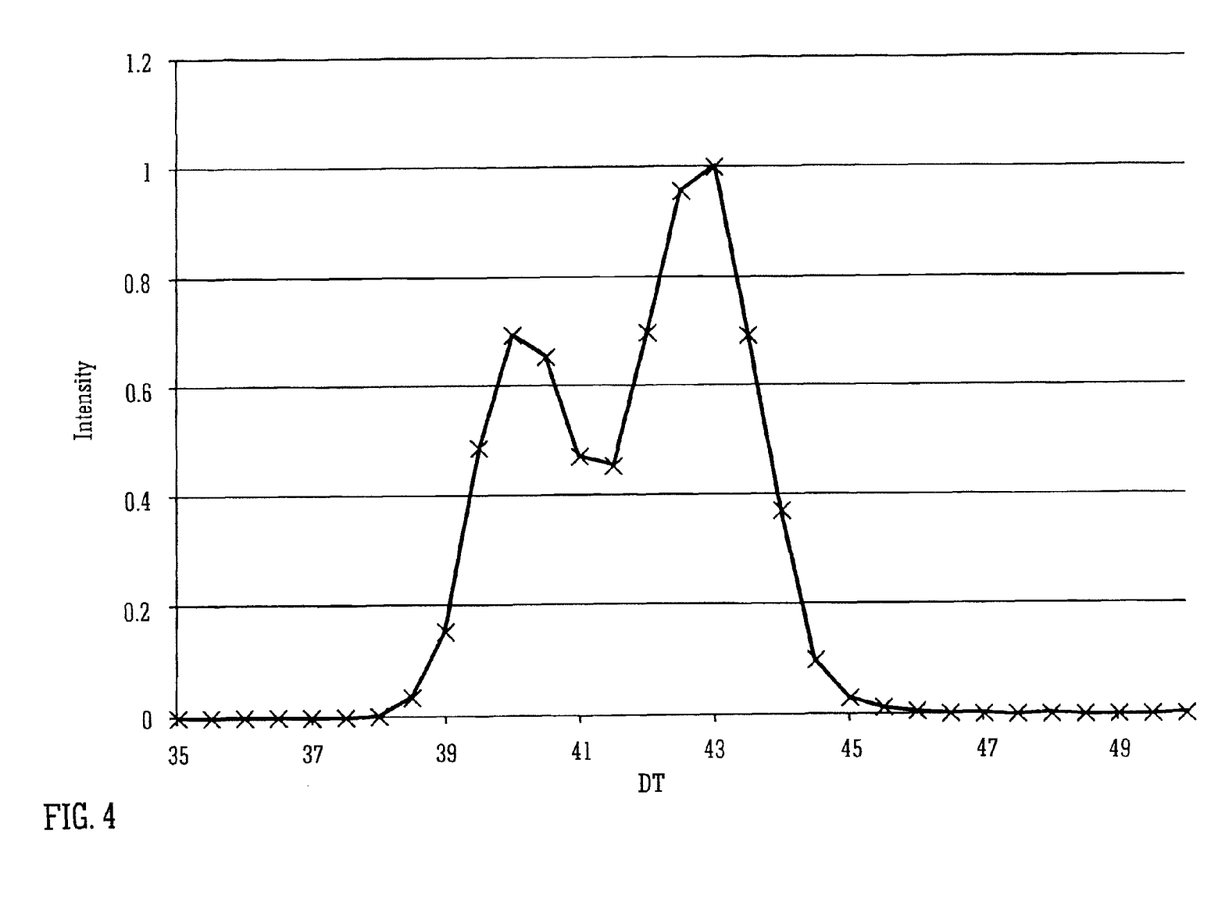
FIG. 4 shows how according to an embodiment mass spectral data obtained without a time delay is combined with mass spectral data obtained with a time delay so as to effectively increase the digitisation of an ion mobility ion peak.

The combined data shown in FIG. 4 appears to be at a higher digitisation rate than data obtained in a conventional manner and as shown in FIG. 2.

Figure 5:
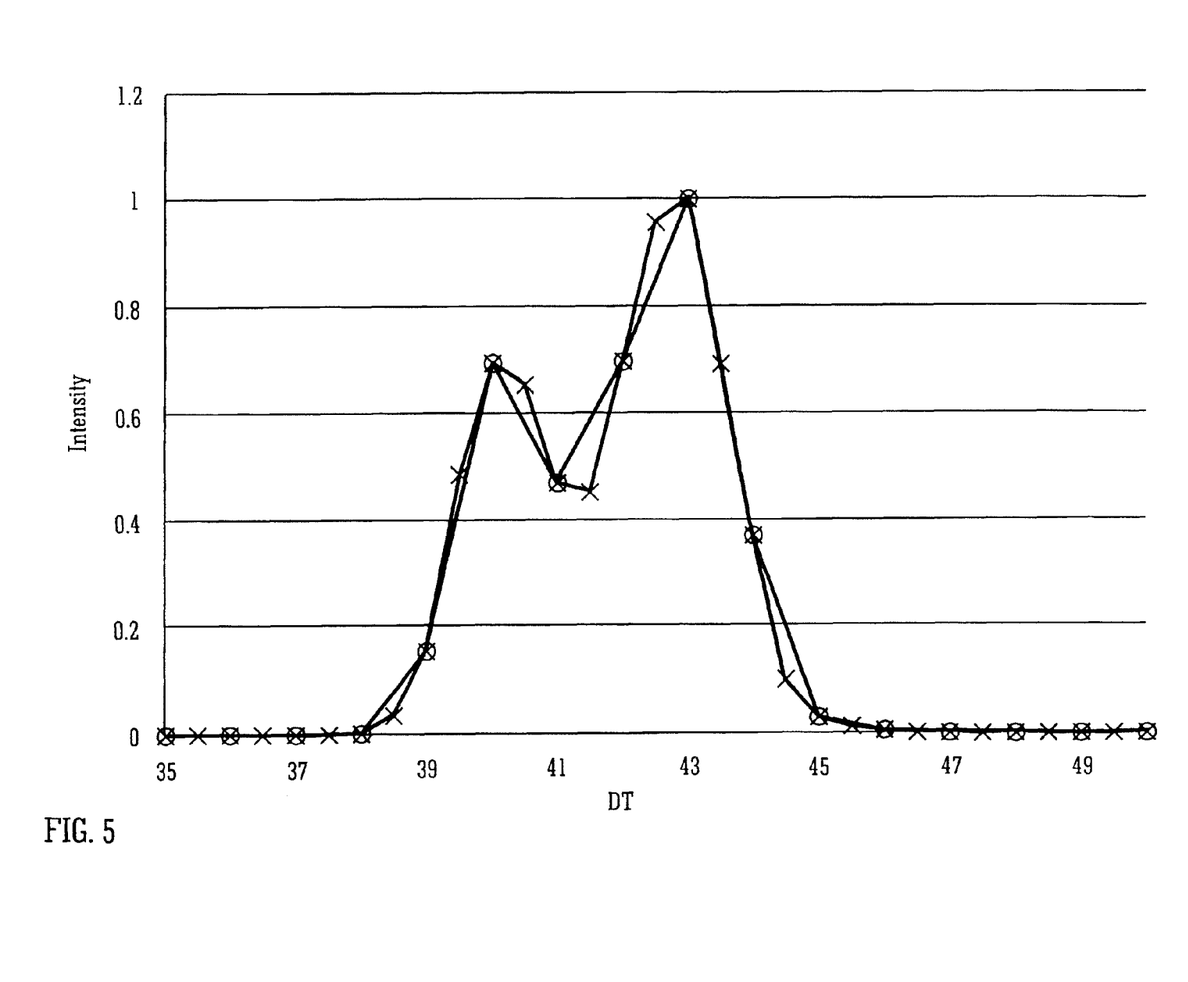
FIG. 5 shows the data shown in FIG. 3 overlapped with the data shown in FIG. 4 to show the improvement in digitisation which is preferably obtained according to a preferred embodiment.

FIG. 5 shows the data shown in FIG. 2 overlapped with the data shown in FIG. 4 and illustrates how the present invention has real benefits in describing the ion mobility spectrometry or separation peak shape and hence improving the resolution.

It should be understood that the approach according to the present invention does not involve operating the pusher electrode any faster but instead is concerned with repeatedly time shifting the ions (i.e. data) which is sampled by the Time of Flight mass analyser.

The above disclosed approach may be applied to ion mobility spectrometry or separation devices with or without pusher synchronisation.

The above described approach may be applied to ion mobility spectrometry or separation devices with or without pre-accumulation.

According to an embodiment more than one time shift may be employed to further improve digitisation.

It is recognised that other separations may benefit from this approach including Capillary Electrophoresis ("CE"), Field Asymmetric Ion Mobility Spectrometry ("FAIMS"), Differential Mobility Spectrometry ("DMS") and time of flight.

The approach according to the preferred embodiment may be utilised with different geometries including IMS-Q-ToF, IMS-ToF and Q-IMS-ToF mass spectrometers.

It is recognised that systems not employing a Time of Flight mass analyser such as ion mobility spectrometry or separation enabled triple quadrupole systems or ion mobility spectrometry or separation enabled ion trap systems may also benefit from the preferred embodiment.

It is recognised that other less preferred approaches other than traveling waves may be used to introduce the time shift such as axial fields.

It is recognised that mobility separators other than linear drift tubes may be used such as travelling wave, non linear drift tubes or time varying field drift tubes.

It is recognised that introducing a shift that varies as a function of drift time or ion mobility (i.e. not just an offset) may have benefit but this is less preferred.

It is recognised that the approach can work in conjunction with other known modes of operation available on orthogonal acceleration Time of Flight mass analysers such as Enhanced Duty Cycle ("EDC") and High Duty Cycle ("HDC") as well as with known other modes of operation available on IMS-Q-ToFs or Q-IMS-ToFs instruments.

It is recognised that the time shift value can either be 'dead reckoned' based on instrument knowledge or more accurately calibrated via a calibration routine.

According to an alternative arrangement the switching may be spatial e.g. the beam could be switched between different channels with different delays.

The higher digitisation can be used to select smaller portions of a total ion mobility spectrometry or separation peak in a nested acquisition.

The present invention has particular applicability on future generations of ion mobility spectrometry or separation enabled instruments Although the present invention has been described with reference to preferred embodiments, it will be understood by those skilled in the art that various changes in form and detail may be made without departing from the scope of the invention as set forth in the accompanying claims.

The invention claimed is:

1. A method of analysing ions comprising:
   (i) separating ions according to a physico-chemical property in a separator;
   (ii) transmitting ions which emerge from said separator through a transfer device with a first transit time t1, energising a pusher electrode or orthogonal acceleration electrode and obtaining first data;
   (iii) transmitting ions which subsequently emerge from said separator through said transfer device with a second greater transit time t2, energising said pusher electrode or orthogonal acceleration electrode and obtaining second data; and
   (iv) repeating steps (ii) and (iii) one or more times;
   wherein said method further comprises:
   energising said pusher electrode or orthogonal acceleration electrode with a period t3, wherein t2-t1 is arranged to equal t3/n and wherein n=2; and
   combining said first and second data to form a composite data set.

2. A method as claimed in claim 1, wherein said physico-chemical property comprises ion mobility or differential ion mobility.

3. A method as claimed in claim 1, wherein said physico-chemical property comprises mass or mass to charge ratio.

4. A method of mass spectrometry comprising a method as claimed in claim 1.

5. An analytical device comprising:
   a separator for separating ions according to a physico-chemical property;
   a transfer device;
   a pusher electrode or orthogonal acceleration electrode;
   an analyser; and
   a control system arranged and adapted:
   (i) to cause ions to separate according to a physico-chemical property in said separator;
   (ii) to transmit ions which emerge from said separator through said transfer device with a first transit time t1, to energise said pusher electrode or orthogonal acceleration electrode and to analyse said ions with said analyser to obtain first data;
   (iii) to transmit ions which subsequently emerge from said separator through said transfer device with a second greater transit time t2, to energise said pusher electrode or orthogonal acceleration electrode and to analyse said ions with said analyser to obtain second data; and
   (iv) to repeat steps (ii) and (iii) one or more times;
   wherein said control system is further arranged and adapted:
   to energise said pusher electrode or orthogonal acceleration electrode with a period t3, wherein t2-t1 is arranged to equal t3/n and wherein n=2; and
   to combine said first and second data to form a composite data set.

6. An analytical device as claimed in claim 5, wherein said separator comprises an ion mobility spectrometer, a differential ion mobility spectrometer or other separation device.

7. An analytical device as claimed in claim 5, wherein said separator comprises a device for separating ions according to their mass or mass to charge ratio.

8. An analytical device as claimed in claim 5, further comprising a device arranged and adapted to pulse ions into said separator.

9. An analytical device as claimed in claim 5, wherein said analyser comprises an orthogonal acceleration Time of Flight mass analyser having a pusher electrode or an orthogonal acceleration electrode.

10. An analytical device as claimed in claim 9, wherein said pusher electrode or orthogonal acceleration electrode is energised asynchronously with respect to said separator.

11. A mass spectrometer comprising an analytical device as claimed in claim 5.

12. A method of analysing ions comprising:
   (i) separating ions according to a physico-chemical property in a separator;
   (ii) transmitting ions which emerge from said separator through a first ion path with a first transit time t1, energising a pusher electrode or orthogonal acceleration electrode and obtaining first data;
   (iii) transmitting ions which subsequently emerge from said separator through a second different ion path with a second greater transit time t2, energising said pusher electrode or orthogonal acceleration electrode and obtaining second data; and
   (iv) repeating steps (ii) and (iii) one or more times;
   wherein said method further comprises:
   energising said pusher electrode or orthogonal acceleration electrode with a period t3, wherein t2-t1 is arranged to equal t3/n and wherein n=2; and
   combining said first and second data to form a composite data set.

13. A method of mass spectrometry comprising a method as claimed in claim 12.

14. An analytical device comprising:
   a separator for separating ions according to a physico-chemical property;
   a transfer device;
   a pusher electrode or orthogonal acceleration electrode;
   an analyser; and
   a control system arranged and adapted:

(i) to cause ions to separate according to a physico-chemical property in said separator;

(ii) to transmit ions which emerge from said separator through a first ion path through said transfer device with a first transit time t1, to energise said pusher electrode or orthogonal acceleration electrode and to analyse said ions with said analyser to obtain first data;

(iii) to transmit ions which subsequently emerge from said separator through a second different ion path through said transfer device with a second greater transit time t2, to energise said pusher electrode or orthogonal acceleration electrode and to analyse said ions with said analyser to obtain second data; and (iv) to repeat steps (ii) and (iii) one or more times;

wherein said control system is further arranged and adapted:

to energise said pusher electrode or orthogonal acceleration electrode with a period t3, wherein t2-t1 is arranged to equal t3/n and wherein n=2; and to combine said first and second data to form a composite data set.

15. A method of analysing ions comprising:

(i) separating ions according to a physico-chemical property in a separator during a first cycle of separation and transmitting ions which emerge from said separator through a transfer device with a first transit time t1, energising a pusher electrode or orthogonal acceleration electrode and obtaining first data;

(ii) separating ions according to said physico-chemical property in said separator during a second separate cycle of separation and transmitting ions which subsequently emerge from said separator through said transfer device with a second greater transit time t2, energising said pusher electrode or orthogonal acceleration electrode and obtaining second data; and (iii) repeating steps (i) and (ii) one or more times;

wherein said method further comprises:

energising said pusher electrode or orthogonal acceleration electrode with a period t3, wherein t2-t1 is arranged to equal t3/n and wherein n=2; and combining said first and second data to form a composite data set.

16. An analytical device comprising:

a separator for separating ions according to a physico-chemical property;

a transfer device;

a pusher electrode or orthogonal acceleration electrode;

an analyser; and a control system arranged and adapted:

(i) to cause ions to separate according to a physico-chemical property in said separator during a first cycle of separation and to transmit ions which emerge from said separator through said transfer device with a first transit time t1, to energise said pusher electrode or orthogonal acceleration electrode and to analyse said ions with said analyser to obtain first data;

(ii) to cause ions to separate according to a physico-chemical property in said separator during a second separate cycle of separation and to transmit ions which subsequently emerge from said separator through said transfer device with a second greater transit time t2, to energise said pusher electrode or orthogonal acceleration electrode and to analyse said ions with said analyser to obtain second data; and (iii) to repeat steps (i) and (ii) one or more times; and wherein said control system is further arranged and adapted:

to energise said pusher electrode or orthogonal acceleration electrode with a period t3, wherein t2-t1 is arranged to equal t3/n and wherein n=2; and to combine said first and second data to form a composite data set.

* * * * *